United States Patent
Takehara

[19]

[11] Patent Number: 6,163,952
[45] Date of Patent: Dec. 26, 2000

[54] METHOD OF MANUFACTURING ARMATURE OF MOTOR USING HOOP MEMBER

[75] Inventor: Isamu Takehara, Narashino, Japan

[73] Assignee: Seiko Seiki Kabushiki Kaisha, Japan

[21] Appl. No.: 08/964,589

[22] Filed: Nov. 5, 1997

[30] Foreign Application Priority Data

Nov. 6, 1996 [JP] Japan ................................. 8-310201

[51] Int. Cl.[7] .......................... H02K 15/02; H02K 1/12
[52] U.S. Cl. ................................ 29/598; 29/596; 29/605; 29/606; 29/607; 310/264; 310/259; 310/218; 310/216
[58] Field of Search .......................... 29/596, 598, 605, 29/606, 607, 609, 735; 310/264, 269, 254, 259, 218, 216, 44

[56] References Cited

U.S. PATENT DOCUMENTS

| | | | |
|---|---|---|---|
| 3,914,859 | 10/1975 | Pierson | 29/596 |
| 4,193,281 | 3/1980 | Kulikov et al. | 29/596 |
| 4,350,914 | 9/1982 | Searle | 310/194 |
| 4,372,035 | 2/1983 | McMillen | 29/596 |
| 4,438,558 | 3/1984 | Mitsui | 29/598 |
| 4,464,595 | 8/1984 | Hamano et al. | 29/596 |
| 4,602,423 | 7/1986 | Ulrich et al. | 29/596 |
| 4,643,346 | 2/1987 | Gotoh | 29/596 |
| 4,712,035 | 12/1987 | Forbes et al. | 29/596 |
| 5,319,844 | 6/1994 | Huang et al. | 29/605 |
| 5,481,143 | 1/1996 | Burdick | 310/68 B |
| 5,570,503 | 11/1996 | Stokes | 29/596 |
| 5,722,152 | 3/1998 | Sumi et al. | 29/596 |

FOREIGN PATENT DOCUMENTS 217597  5/1925  United Kingdom .

*Primary Examiner*—Lee Young
*Assistant Examiner*—A. Dexter Tugbang
*Attorney, Agent, or Firm*—Adams & Wilks

[57] ABSTRACT

A motor armature having a simplified assembly comprises an inner cylinder and an outer cylinder arranged coaxially, and a plurality of pole pieces provided radially at equal intervals between the inner and outer cylinders. The inner cylinder is formed into a cylindrical shape by curling up in the longitudinal direction a first hoop member (band steel) formed of a magnetic material and having a predetermined thickness and length. The outer cylinder is formed of a second hoop member similar to the first hoop member. The pole pieces each comprise a wire piece cut from a wire formed of a magnetic material and having a coil would thereon. One end of each pole piece is welded to one of the hoop members and the other end of the pole pieces is welded to the other hoop member.

34 Claims, 12 Drawing Sheets

METHOD OF MANUFACTURING ARMATURE OF MOTOR USING HOOP MEMBER

BACKGROUND OF THE INVENTION

1. Field of the Invention

The present invention relates to a motor armature used in motors such as a brushless motor, to a manufacturing method thereof and to a motor having the same.

2. Background Discussion

Heretofore, as an armature used for a brushless motor and the like, there have been known one fabricated by winding a coil around an iron core made by laminating a plurality of punched steel plates or one fabricated by winding a coil around an iron core made by laminating a plurality of punched steel plates which are divided into a plurality of pieces and by cylindrically connecting each core around which the coil is wound.

However, the armature fabricated by winding the coil around the iron core made by laminating a plurality of punched steel plates has problems in that its overall structure is complicated in general and it is difficult to wind the coil around the core.

Meanwhile, the armature fabricated by winding the coil around the iron core made by laminating a plurality of punched steel plates which are divided into a plurality of pieces and by cylindrically connecting each core around which the coil is wound has a problem in that although it is easy to wind the coil around the core, the assembly work thereof for connecting cylindrically each core piece around which the coil is wound is difficult.

SUMMARY OF THE INVENTION

Accordingly, it is a primary object of the present invention to provide a motor armature whose simplified assembly can be facilitated and which can be miniaturized and thinned.

A secondary object of the present invention is to provide manufacturing methods for the armature which facilitate and readily automate the assembly thereof.

In order to achieve the primary object, a motor armature of the present invention comprises a plurality of pole pieces each comprising a coil wound around a rod made of a magnetic material; and a cylinder formed of a magnetic material which is fixed with the plurality of pole pieces disposed radially at equal intervals at a position spaced from the center of the cylinder by a predetermined distance on at least one side of the center side or the outer periphery side thereof.

The above-mentioned cylinder is formed by curling up a hoop member formed of a magnetic material and the rod is a wire piece obtained by cutting a wire formed of a magnetic material.

Because the armature of the present invention is simply constructed as described above, it allows the assembly work to be facilitated and the miniaturization, thinning and reduction of cost to be realized, Further, it allows changes in the size and structure of the armature to be made readily and swiftly.

In order to achieve the secondary object, a method for manufacturing the inventive motor armature comprises a first step of creating a plurality of pole pieces each comprising a coil wound around a wire piece 5 formed of a magnetic material; a second step of fixing one end of the plurality of pole pieces created in the first step to one and the same plane of a first hoop member made of a magnetic material at equal intervals; and a third step of creating a cylinder attached with pole pieces by curling up the first hoop member to which the plurality of pole pieces are fixed in the second step so that the plurality of pole pieces are inside or outside the cylinder.

Further, in parallel with creating the cylinder attached with the pole pieces by curling up the first hoop member to which the plurality of pole pieces are attached so that the plurality of pole pieces come outside the cylinder in the third step described above, an outer cylinder may be created while fixing an exposed end of the each of pole pieces with a second hoop member.

Further, an inventive method for manufacturing the motor armature comprises a first step of creating a plurality of pole pieces each comprising a coil wound around a wire piece formed of a magnetic material; and a second step of fixing one end of the plurality of pole pieces created in the first step either to the inner peripheral face or the outer peripheral face of a first cylinder formed by curling up a hoop member made of a magnetic material radially at equal intervals.

Further, in the second step described above, it is possible to arrange the armature such that a second outer cylinder coaxial with first the cylinder having the pole pieces is fixed with an open end of each of the plurality of pole pieces fixed to the first cylinder after creating the first cylinder with the pole pieces attached thereto by curling up the hoop member so that the plurality of pole pieces come outside.

Thus, the rod (wire piece) and the hoop members are used in the inventive method for manufacturing the armature. This allows the automation to be facilitated and to deal with changes in the size and structure of the armature swiftly by changing the thickness of the wire piece and the thickness of the hoop member.

DESCRIPTION OF THE PREFERRED EMBODIMENT(S)

Preferred modes of a motor armature of the invention and manufacturing methods thereof will be explained below in detail with reference to FIGS. 1 through 13, FIG. 1 is a perspective view of the armature according to a first preferred embodiment.

Figure 1:
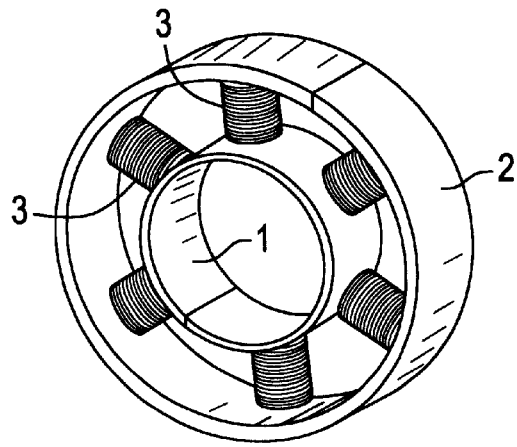
FIG. 1 is a perspective view showing an embodiment of an armature of the present invention.

As shown in FIG. 1, this armature is constructed by disposing coaxially an inner cylinder 1 and an outer cylinder 2 and by providing a plurality of pole pieces 3 radially at equal intervals between the inner cylinder 1 and the outer cylinder 2.

The inner cylinder 1 is formed into a cylindrical shape by curling up in the longitudinal direction a hoop member (band steel) which is formed of a magnetic material and which has a predetermined thickness and length and by jointing the both ends thereof by welding or the like.

Similarly to the inner cylinder 1, the outer cylinder 2 is formed into a cylindrical shape by curling up in the longitudinal direction a hoop member (band steel) which is formed of a magnetic material and which has a predetermined thickness and length and by jointing the both ends thereof by welding or the like.

Figure 2:
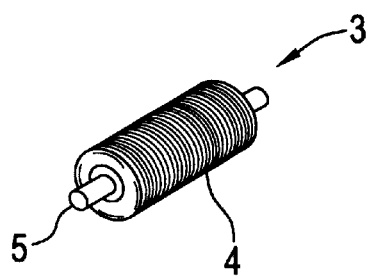
FIG. 2 is a perspective view showing a structure of a pole piece.

As shown in FIG. 2, the pole piece 3 consists of a wire piece 5 obtained by cutting a wire (wire rod) which is made of a magnetic material and which has a predetermined thickness into a predetermined length and a coil 4 wound around the wire piece 5. One end of the wire piece 5 is fixed to the outer peripheral face of the inner cylinder 1 by welding or the like and the other end of the wire piece 5 is fixed to the inner peripheral face of the outer cylinder 2.

While the plurality of pole pieces 3 are provided between the inner cylinder 1 and the outer cylinder 2, the number thereof is determined depending on the design and specifications of the motor, in which the armature is to be used and may be, for instance, three, six, eight, nine or twelve, Because the wire piece 5 is obtained by cutting a wire and its cross-sectional shape is the same (circular) in the longitudinal direction, there is a merit in that the coil 4 can be readily wound by a coil winding machine. However, the shape of the wire piece 5 is not limited only to such shape, and it is possible to provide fixing sections like convex sections at the both ends thereof so as to insert the convex sections to fixing holes provided on the inner cylinder 1 and the outer cylinder 2.

Further, the sectional shape of the wire piece 5 in the longitudinal direction is not limited to circular, and it may instead be triangular or square, for example. Still more, the wire piece 5 may be formed by laminating thin plate-like members.

Figure 3:
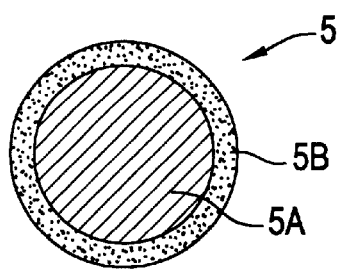
FIG. 3 is a sectional view showing a section of a wire piece.

Next, the internal structure of the wire piece 5 will be explained with reference to FIG. 3.

The wire piece 5 is composed of a center layer 5A whose section is circular and a skin layer 5B which is formed so as to have a constant thickness around the center layer 5A.

The center layer 5A is made of low carbon steel or pure iron which are magnetic materials having high saturation magnetic flux density. The skin layer 5B is made of Fe—Co alloy, Fe—Ni alloy or amorphous alloy which are magnetic materials having high magnetic permeability and causing less iron loss. The reason why the wire piece 5 is composed of the two layers, using the magnetic materials having different natures, will be explained below.

Figure 4:
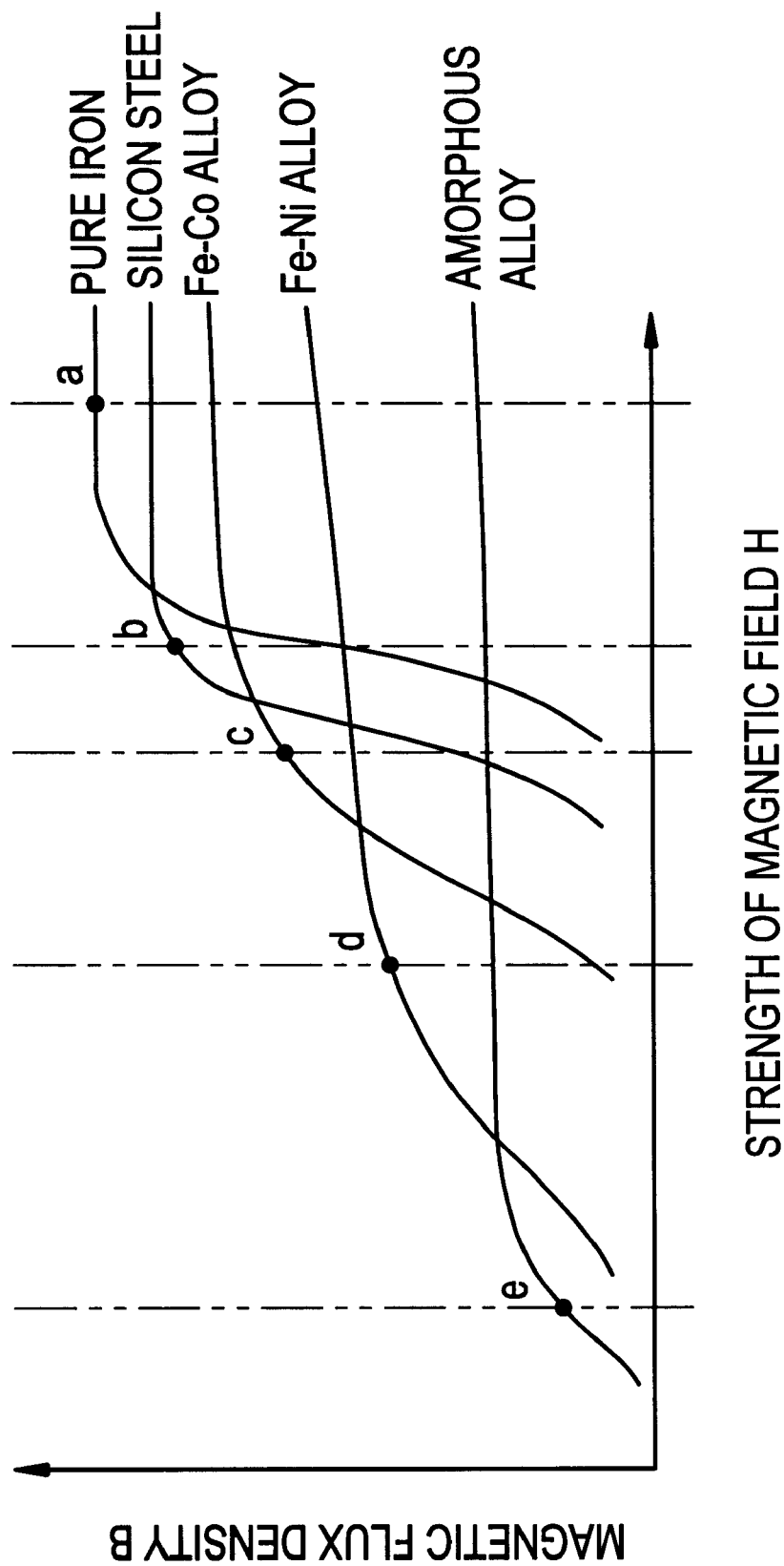
FIG. 4 is a magnetic characteristic chart of magnetic materials.
Figure 5:
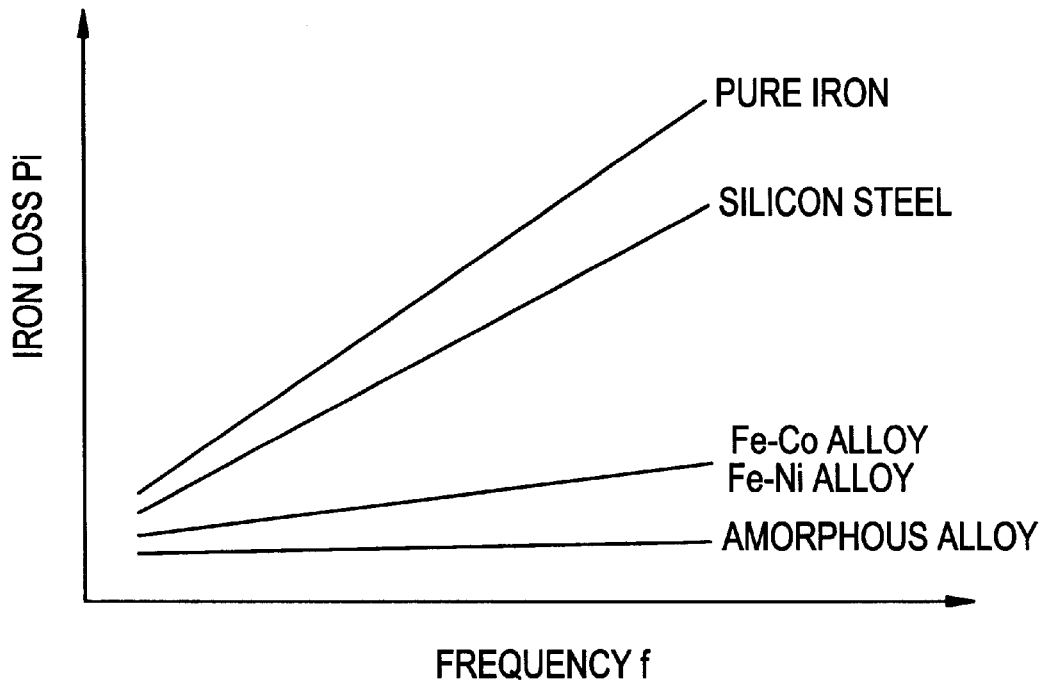
FIG. 5 is a frequency characteristic chart of the magnetic materials.
Figure 6:
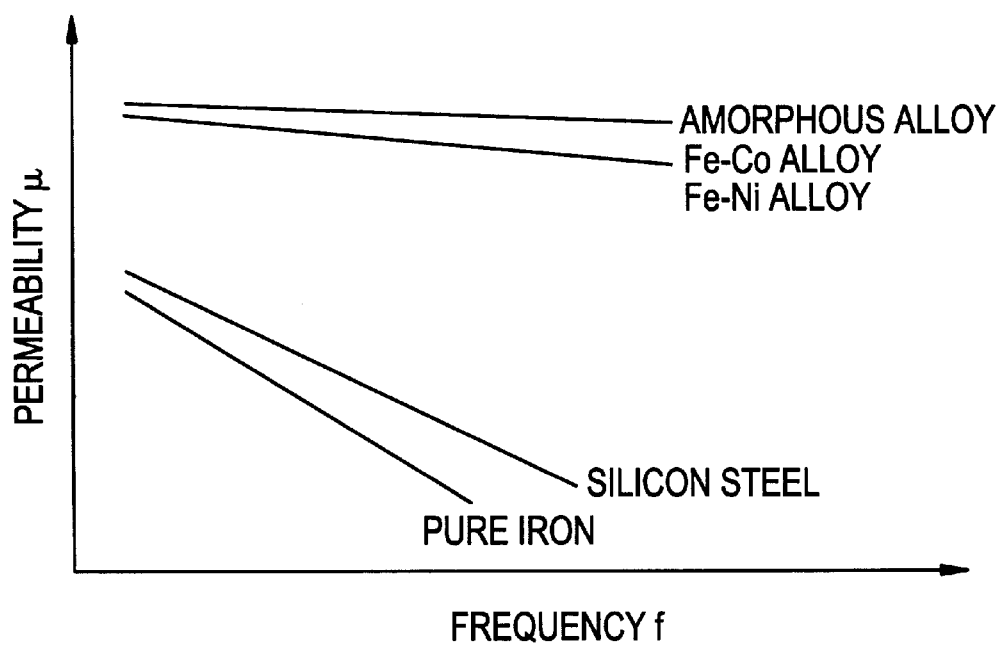
FIG. 6 is a frequency characteristic chart of permeability.

FIG. 4 is a magnetic characteristic chart of various magnetic materials. FIG. 5 is a frequency characteristic chart of iron loss the magnetic materials. FIG. 6 is a frequency characteristic chart of permeability of the magnetic materials. According to FIG. 4, when the strength of magnetic field is determined in order of a, b, c, d and e, the flux density corresponding to that is determined accordingly.

When the armature of the present embodiment is used in a motor, there is no substantial difference in the iron loss of the various magnetic materials in activating the motor because alternating frequency is low as shown in FIG. 5. Accordingly, the pure iron and silicon steel, which can be readily worked, are well suited. Further, because a large torque is required in activating the motor and a large current flows through the coil, increasing the strength of the magnetic field, the pure iron and the silicon steel, which are the magnetic materials having the high saturation magnetic flux density as shown in FIG. 4, are well suited.

When the motor rotates at high speed after the activation on the other hand, the alternating frequency of the magnetic flux becomes high. In this case, although the iron loss of the pure iron and the like increases remarkably in correspondence to the increase of the frequency, the iron loss of the amorphous alloy and the like does not increase so much in correspondence to the increase of the frequency, and the Fe—Co alloy, Fe—Ni alloy or amorphous alloy are well suited. Further, as the strength of the magnetic field is reduced, because the current flowing through the coil decreases during the high speed rotation of the motor after the activation, a material having relatively high saturation magnetic flux density is suited, even though the strength of the magnetic field is small, like the Fe—Co alloy, Fe—Ni alloy or amorphous alloy as shown in FIG. 4.

Thus, the magnetic materials suited as the wire piece 5 are mutually contradictory in activating the motor and in rotating it at high speed after the activation and it is difficult to cover the whole range from the activation to the high speed rotation of the motor by use of a single one of the magnetic materials. Therefore, it is conceivable to combine the two materials having different characteristics.

In addition, during the high speed rotation of the motor after the activation, the alternating frequency of the magnetic flux is high so that it causes a skin effect of the magnetic flux. As result, the magnetic flux density of the wire piece 5 on the skin side increases so that the wire piece 5 undergoes less iron loss at the center side thereof and large iron loss at the skin side thereof.

Accordingly, it is preferable to make the skin side of the wire piece 5 by the Fe—Co alloy, Fe—Ni alloy or amorphous alloy which experiences less iron loss even when the frequency is high, as shown in FIG. 5, in order to minimize the large iron loss at the skin side caused by the skin effect.

Then, it is preferable to make the center layer 5A of the wire piece 5 by the low carbon steel or pure iron, which are magnetic materials having high saturation magnetic flux density, and to make the skin layer 5B by the Fe—Co alloy, Fe—Ni alloy, or amorphous alloy which are the magnetic materials having high magnetic permeability and causing less iron loss.

By composing the wire piece 5 as described above, a loss caused by the iron loss may be reduced across the whole range from activation to high speed rotation of the motor. It also allows a magnetic flux necessary for driving to be obtained mainly by the center layer 5A part in activating the motor and a magnetic flux necessary for rotation to be obtained mainly by the skin part 5A in rotating the motor at high speed.

Further, the iron loss caused by the skin effect of the magnetic flux may be reduced even if a number of rotation of the motor is increased from several thousands of rpm to ten or more thousands of rpm by composing the wire piece 5 as described above.

The armature of the present mode constructed as described above may be used by combining either an inner rotor or an outer rotor made of permanent magnet for example.

Further, the armature of the present invention may be constructed so that the outer cylinder 2 is removed from the armature shown in FIG. 1 (armature which is composed of the pole pieces 3 and the inner cylinder 1). In this case, the armature is used by combining with an outer rotor.

Still more, the armature of the present invention may be constructed so that the inner cylinder 1 is removed from the armature shown in FIG. 1 (armature which is composed of the pole pieces 3 and the outer cylinder 2). In this case, the armature is used by combining with an inner rotor.

Methods for manufacturing the armature constructed as described above will be explained below.

Figure 7A:
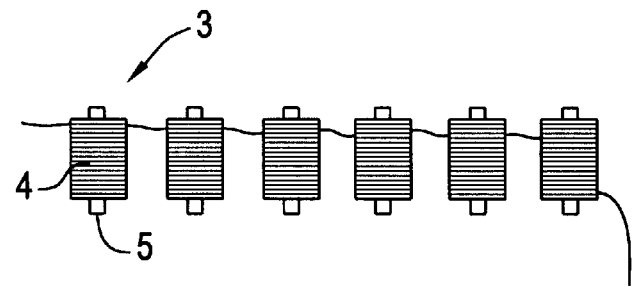
FIG. 7 is a drawing showing steps of a first method for manufacturing of the armature.
Figure 7B:
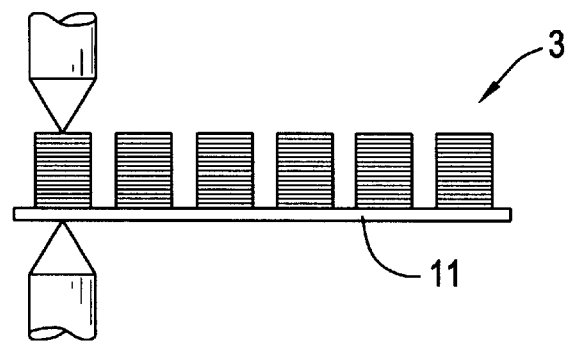
Figure 7C:
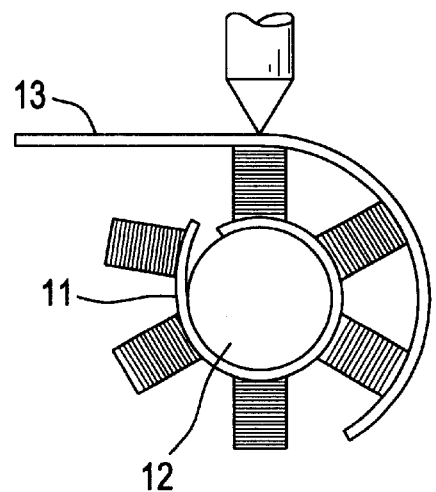

FIGS. 7(A)–7(C) are is a process drawings for explaining a first method for manufacturing the armature.

In the first manufacturing method, the coil 4 is wound as described later around the wire pieces 5 which are obtained by cutting a wire made of a magnetic material into a predetermined length to create the plurality of pole pieces 3 as shown in FIG. 7(A). Here, six pole pieces 3 are created.

Next, one end of each wire piece 5 of the plurality of pole pieces 3 is fixed to a first hoop member 11 which has been cut into a predetermined length beforehand at equal intervals by joint means such as spot welding or caulking as shown in FIG. 7(B).

Then, in parallel with creating the inner cylinder by winding the first hoop member 11 around a core 12, each of the other end of the wire piece 5 of the pole pieces 3 is fixed to a second hoop member 13 by means of spot welding or caulking to create the outer cylinder as shown in FIG. 7(C). Then, the armature as shown in FIG. 1 is completed.

It is noted that in FIG. 7(C), the inner cylinder may be created in advance by curling up the first hoop member 11 on which the pole pieces 3 are fixed and the outer cylinder may be created thereafter by curling up the hoop member 13 as described above.

It is noted that although the pole piece 3 is created by winding the coil 4 around the wire piece 5 which has been cut in advance in FIG. 7(A), it is also possible, instead of that, to wind the coil 4 at the edge of the continuous wire in advance and to cut the wire into the length of the wire piece 5 after winding the coil 4.

Further, although the one end of the pole piece 3 is fixed to the first hoop member 11 which has been cut in advance in FIG. 7(B), it is also possible, instead of that, to fix one end of the plurality of pole pieces 3 to the first hoop member 11 and to cut the hoop member after finishing the fixation Next, a method for creating the pole pieces 3 by winding the coil around the wire piece explained in FIG. 7(A) will be explained.

Figure 8:
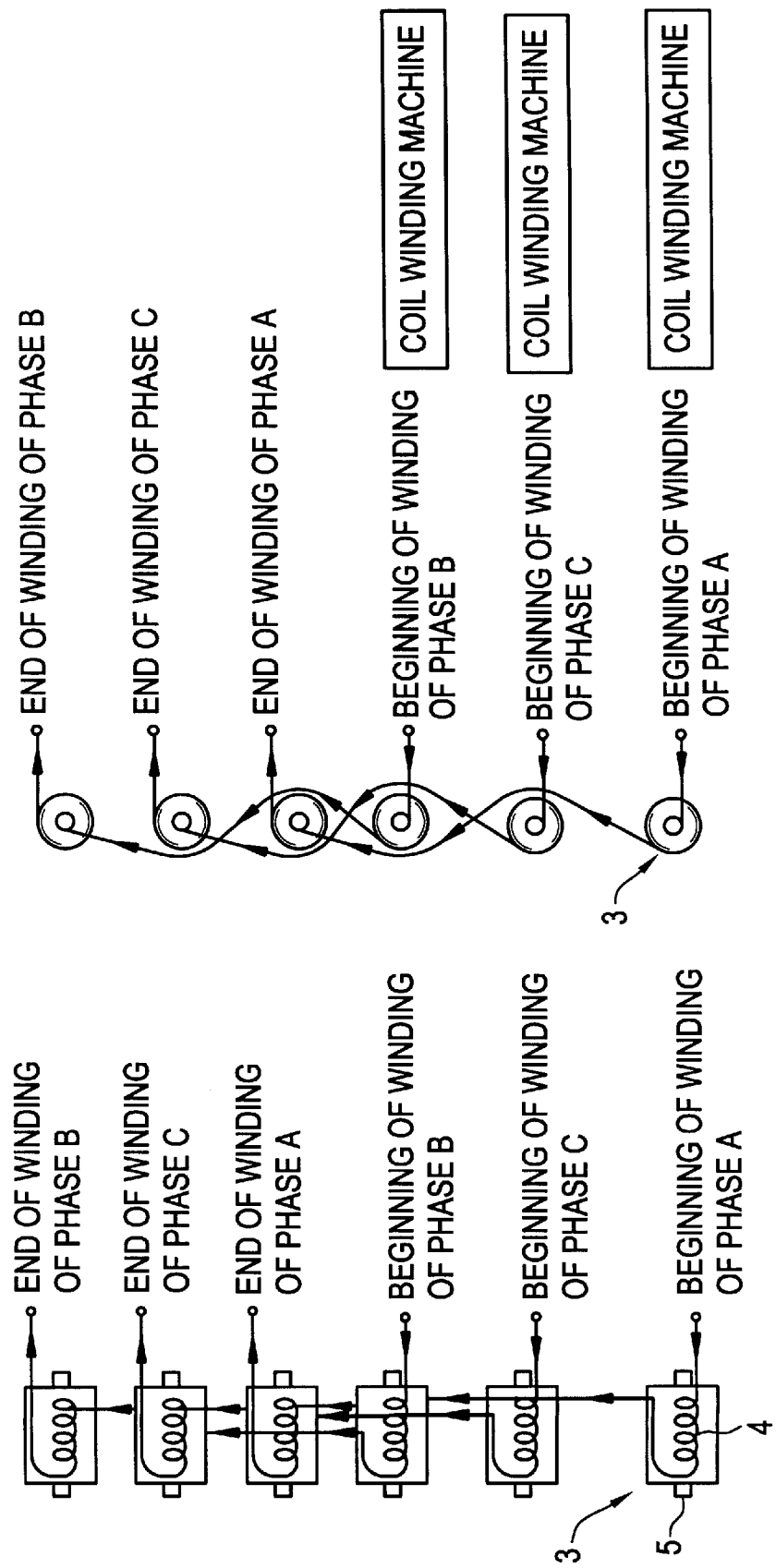
FIG. 8 is a drawing showing a method for creating the pole piece.

FIG. 8 is a drawing diagrammatically showing an embodiment of a method for creating a three-phase coil by using three coil winding machines. In this case, the winding directions of the six pole pieces are all the same. Then, a star connection or a delta connection is made after that.

Figure 9:
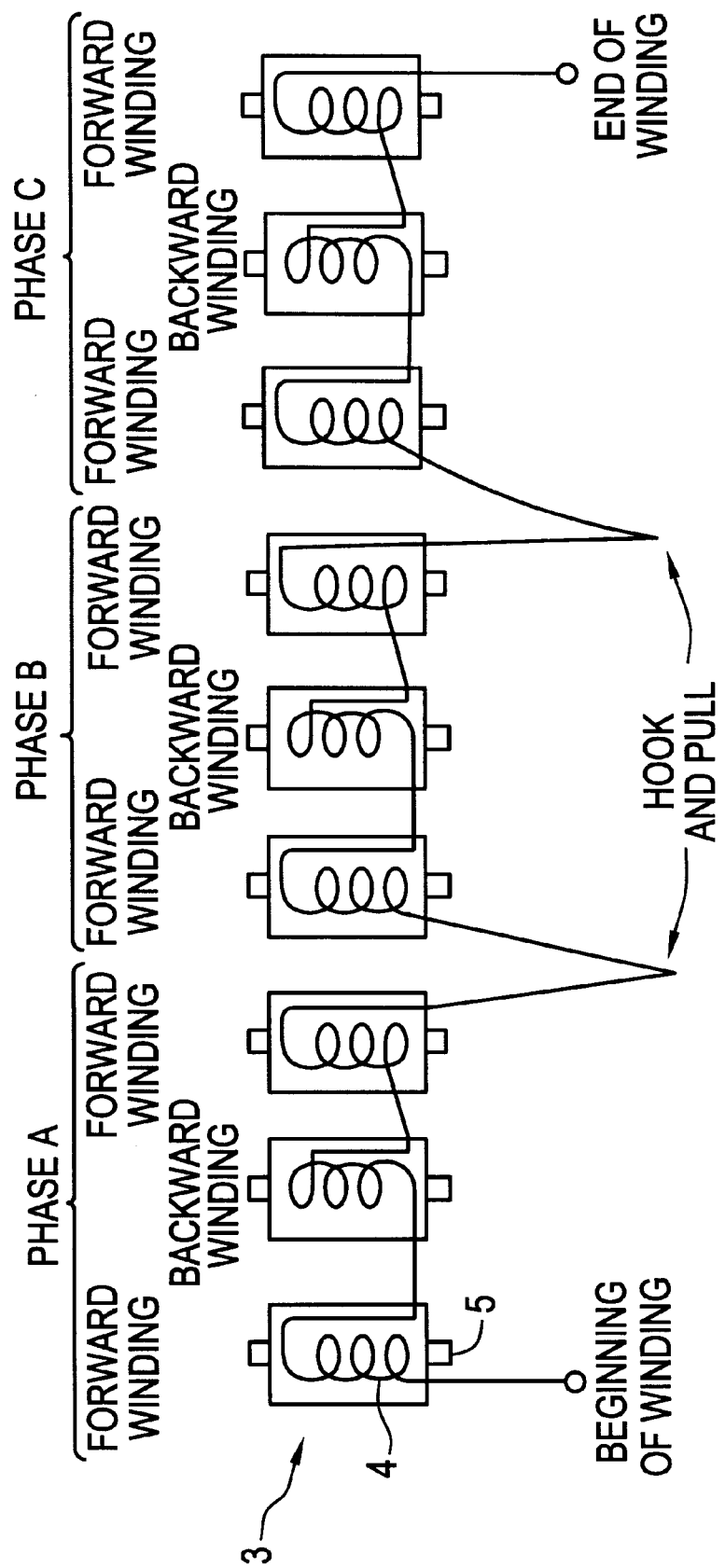
FIG. 9 is a drawing showing another method for creating the pole piece.

FIG. 9 is a drawing diagrammatically showing an embodiment of a method of creating the three-phase coil by using the coil winding machine. In this case, the three poles of each phase of A, B and C are wound forward, backward and forward. A delta connection is made by hooking two spots to connect the beginning and the end of the winding as shown in FIG. 9.

Figure 10:
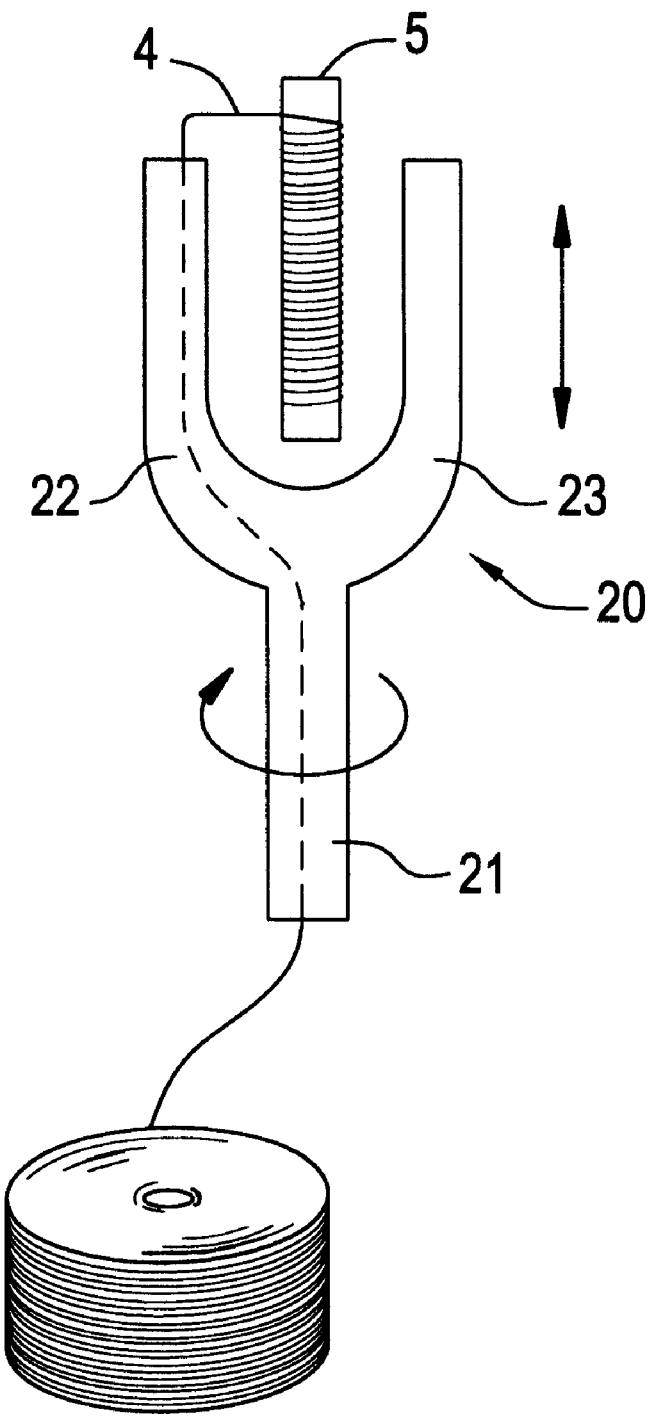
FIG. 10 is a drawing diagrammatically showing a coil winding machine.

FIG. 10 is a drawing diagrammatically showing a coil winder 20 for winding the coil 4 around the wire piece 5. This coil winder 20 comprises a cylindrical base 21, a cylindrical winding section 22 which continues therefrom and bifurcates to the left side of the figure and a balance section 23 which bifurcates to the right side of the figure. It is constructed so that the whole device moves forward and back while turning.

In winding the coil 4 around the wire piece 5, the coil 4 is discharged from an opening at the edge of the winding section 22 via the base 21 and the winding section 22 and the whole coil winder 20 moves forward or back while turning. Thereby, the discharged coil 4 is wound around the wire piece 5. It is noted that the balance section 23 takes a balance when the winding section 22 turns.

By the way, the frequency of rotation of the coil winding machine is around 3000 rpm at most in winding a coil around a prior art armature by means of a special coil winding machine because the structure of the armature is complicated.

However, since the wire piece 5 of the present embodiment is a rod whose section is circular in the longitudinal direction, there is a merit in that the frequency of rotation of the coil winding machine may be increased up to 50,000 to 60,000 rpm in winding the coil 4 by the above-mentioned coil winding machine.

Next, a second method for manufacturing the armature will be explained with reference to process drawings shown in FIGS. 11(A)–11(D).

Figure 11A:
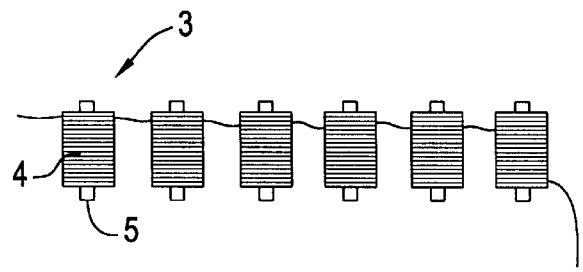
FIG. 11 is a drawing showing steps of a second method for manufacturing of the armature.
Figure 11B:
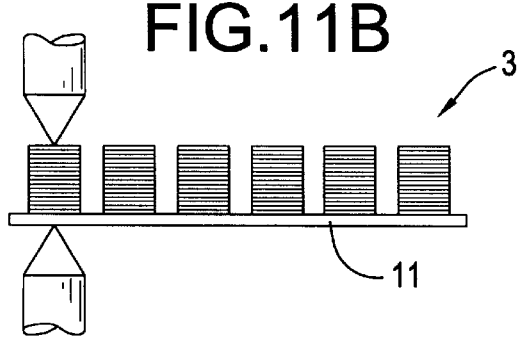

The second manufacturing method is the same with the first manufacturing method up to the steps of creating the plurality of pole pieces 3 in which the coil 4 is wound around the wire piece 5 and of fixing one end of the wire piece 5 of the plurality of pole pieces 3 to the hoop member 11 at equal intervals (see FIGS. 11(A) and 11(B)).

Figure 11C:
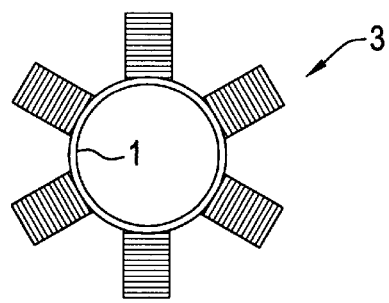

Next, when the hoop member 11 is curled up by winding around the core and the both ends thereof are jointed by welding or the like, the inner cylinder 1 on which the pole pieces 3 are disposed radially is created as shown in FIG. 11(C).

Figure 11D:
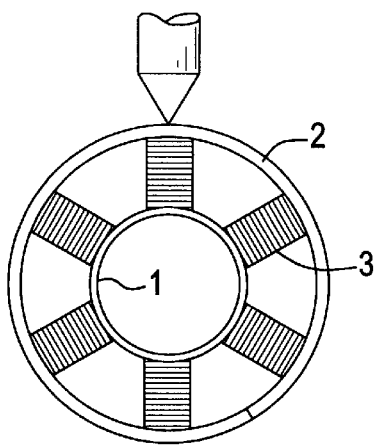

Then, when the outer cylinder 2 made of the hoop member is disposed coaxially with the inner cylinder 1 as shown in FIG. 11(D), the inner peripheral face of the outer cylinder 2 contacts with each other end of the wire piece of the pole piece 3. Each other end of each wire piece is then jointed with the inner peripheral face thereof by means of spot welding or the like, thus completing the armature as shown in FIG. 1.

The armature thus created by the second manufacturing method may be used in combination either with an inner rotor or an outer rotor. The armature in the state in FIG. 11(C) may be used in combination with the outer rotor.

Next, a third method for manufacturing the armature will be explained with reference to process drawings shown in FIG. 12.

Figure 12A:
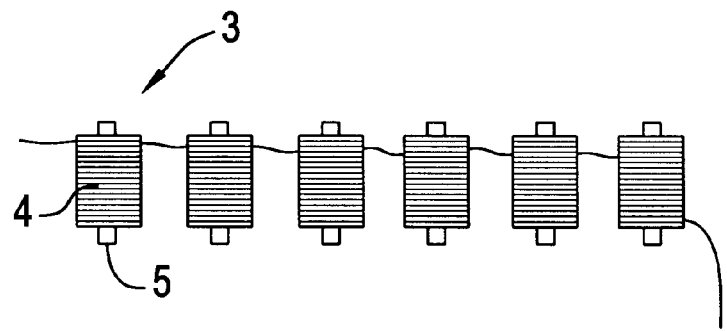
FIG. 12 is a drawing showing steps of a third method for manufacturing of the armature.
Figure 12B:
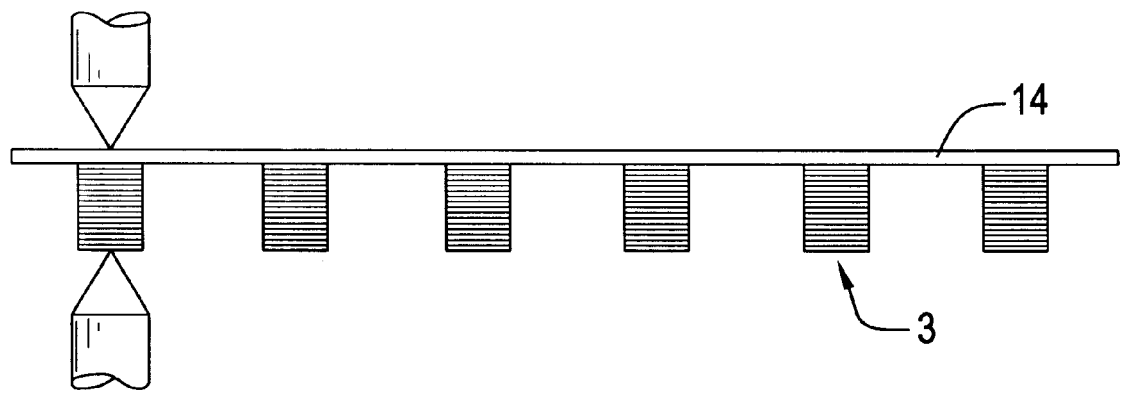

The third manufacturing method is the same with the first manufacturing method up to the steps of creating the plurality of pole pieces 3 in which the coil 4 is wound around the wire piece 5 and of fixing one end of the wire piece 5 of the plurality of pole pieces 3 at equal intervals to a hoop member 14 cut into a predetermined length in advance (see FIGS. 12(A) and 12(B)).

Figure 12C:
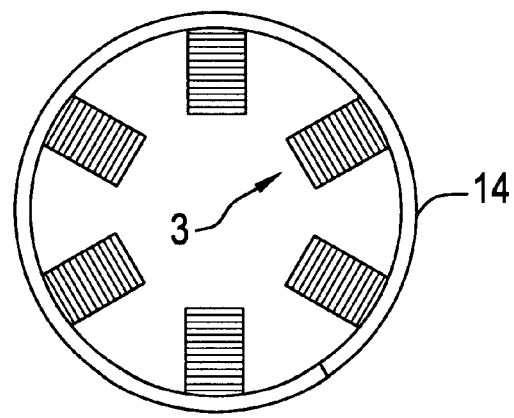

Next, when the hoop member 14 is curled up by winding around the core so that each pole piece 3 comes inside and the both ends thereof are jointed by welding or the like, a cylinder in which the pole pieces 3 are fixed so as to head the center is created as shown in FIG. 12(C). Thus, the armature which can be used in combination with the inner rotor is completed.

Next, a fourth method for manufacturing the armature will be explained with reference to process drawings shown in FIG. 13.

Figure 13A:
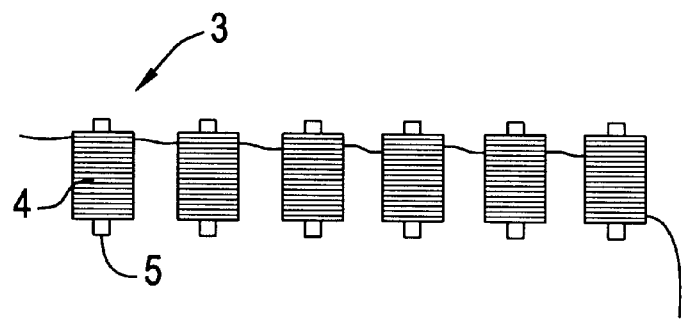
FIG. 13 is a drawing showing steps of a fourth method for manufacturing of the armature.

The fourth manufacturing method is the same with the first manufacturing method up to the step of creating the plurality of pole pieces 3 in which the coil 4 is wound around the wire piece 5 (see FIG. 13(A)).

Figure 13B:
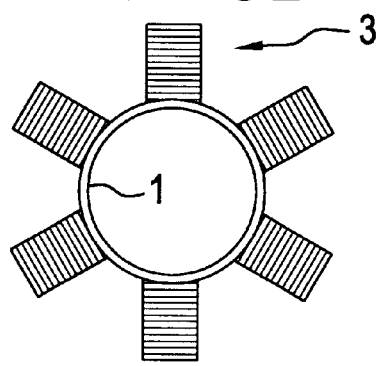

Next, one end of the wire piece 5 of the plurality of pole pieces 3 is fixed radially at equal intervals to the outer peripheral face of the inner cylinder 1 formed by curling up the hoop member as shown in FIG. 13(B) by means of spot welding or caulking.

Figure 13C:
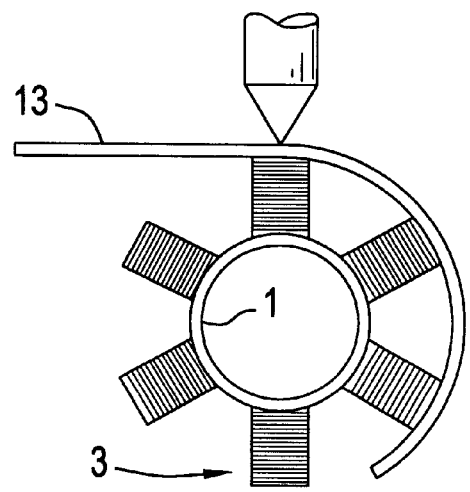

Next, as shown in FIG. 13(C), when the outer cylinder is formed while fixing each other end of the wire piece 5 of the pole piece 3 to the hoop member 13 by means of spot welding or caulking, the armature as shown in FIG. 1 is completed.

It is noted that the plurality of pole pieces 3 in which the coil 4 is wound around the wire piece 5 are created and the wire piece 5 of the plurality of pole pieces 3 are fixed to the outer peripheral face of the inner cylinder 1 which has been formed by curling up the hoop member in the fourth method.

However, it is also possible to create the armature in the state of FIG. 13(B) by fixing the plurality of wire pieces 5 to the hoop member in advance at equal intervals, by creating the inner cylinder 1 by curling up the hoop member on which the wire pieces 5 are fixed and by winding the coil 4 to each wire piece 5 fixed to the inner cylinder 1 at equal intervals.

Next, a fifth method for manufacturing the armature will be explained with reference to process drawings shown in FIG. 14.

Figure 14A:
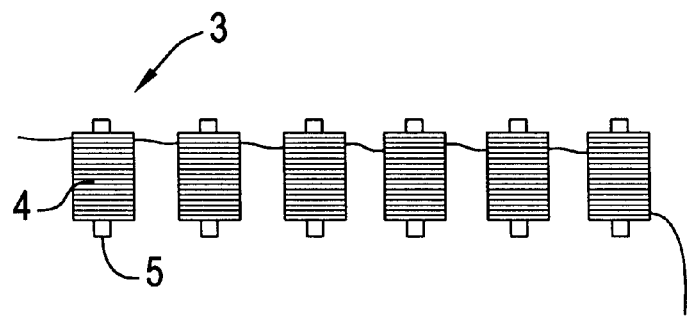
FIG. 14 is a drawing showing steps of a fifth method for manufacturing of the armature.

The fifth manufacturing method is the same with the fourth manufacturing method up to the step of creating the plurality of pole pieces 3 in which the coil 4 is wound around the wire piece 5 (see FIG. 14(A)).

Figure 14B:
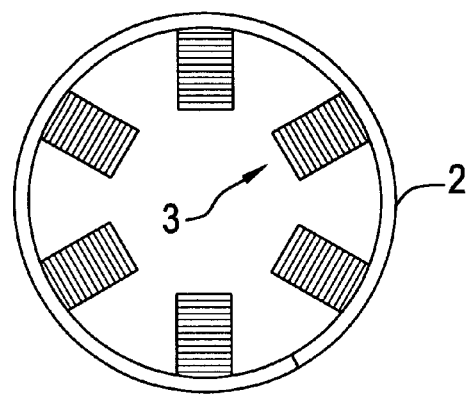

Next, one end of the wire piece 5 of each pole piece 3 is jointed to the inner peripheral face of the outer cylinder 2 created by curling up the hoop member so that each pole piece 3 heads the center by means of spot welding or caulking as shown in FIG. 14(B).

Figure 14C:
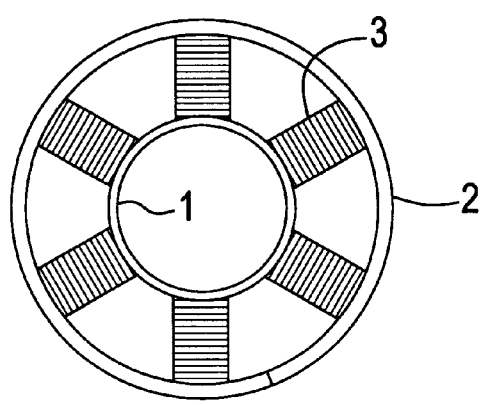

Next, when the inner cylinder 1 made of the hoop member is disposed coaxially with the outer cylinder 2 as shown in FIG. 14(C), the outer peripheral face of the inner cylinder 1 contacts with each other end of the wire piece of the pole piece 3. Then, each other end of each wire piece is jointed with the outer peripheral face by means of spot welding or caulking, thus completing the armature as shown in FIG. 1.

Figure 15:
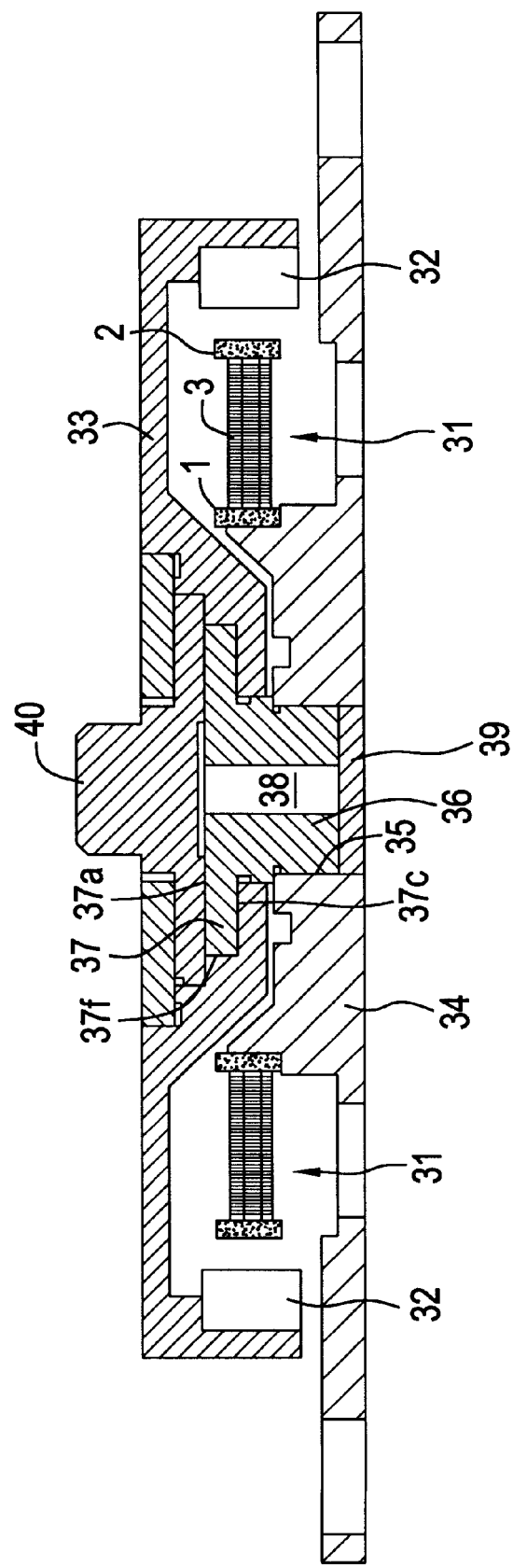
FIG. 15 is a section view showing a spindle motor having a motor armature as shown in FIG. 1.

FIG. 15 is a sectional view of a high speed spindle motor using a motor armature shown in FIG. 1.

a stator 31 which is formed by winding wirings around an iron core, namely, a motor armature is mounted at a position facing the magnet 32 mounted on the inner circumferential surface of the bottomed rotor 33 on the outer circumferential side of the stationary base 34.

In this embodiment, there is provided a stationary base11.

A central hole 35 is formed at the center of the stationary base11 a lower portion of cylindrical stationary shaft 36 is press-fitted into the central hole 35.

A central hole 35 is formed at the center of the stationary base 34. A lower portion of a cylindrical stationary shaft 13 is press-fitted into the central hole 35.

As shown in FIG. 15, a flange disc 37 for the bearing is provided coaxially with the stationary shaft 36 in the upper portion of the stationary shaft 36. Although this flange disc 15 is formed integrally with the stationary shaft 36, instead thereof, the flange disc 37 may be formed discretely from the stationary shaft 36 and may be coupled therewith by a suitable means.

An oil feed hole 38 for feeding oil is provided in the axial direction of the inner central portion of the stationary shaft 36. An opening of the oil feed hole 38 may be covered by a sealing cover 39 after the replenishment of the oil.

An outer circumferential surface of the flange disc 37 is formed as a radial dynamic pressure bearing portion 37f for supporting in the radial direction the rotary member composed of a bottomed rotor 33 and a thrust retaining portion 40.

The top surface and the bottom surface of the flange disc 37 are formed into thrust dynamic pressure bearing portions 37a and 37c, respectively, for supporting in the axial direction the rotary member composed of the bottomed rotary 33 and the thrust retaining portion 40, Because the armature of the present invention is structured as described above, the assembly works can be facilitated, it can be miniaturized and thinned and its cost can be reduced. In addition to that, it allows to deal with changes in size and structure thereof flexibly when there is such change.

Further, because the rod (wire piece) and the hoop members are used in the manufacturing methods of the inventive armature, it facilitates the automation and allows to deal with changes in size and structure of the armature swiftly where there is such change by changing the thickness of the wire piece or the thickness of the hoop member.

What is claimed is:

1. A method for manufacturing a motor armature, comprising the steps of:

a first step of creating a plurality of pole pieces each comprising a coil wound around a wire piece formed of a magnetic material;

a second step of fixing a first end of each of the plurality of pole pieces created in the first step to a first surface of a hoop member formed of a magnetic material such that the pole pieces are spaced by equal intervals by welding;

a third step of creating a cylinder attached to the pole pieces by curling up the hoop member to which the plurality of pole pieces are fixed in the second step into the cylinder so that the plurality of pole pieces are fixed to the cylinder such that the cylinder is an inner cylinder of the motor armature; and a fourth step of forming an outer cylinder simultaneously with formation of the inner cylinder by attaching a second end of each of the pole pieces to a second hoop member by welding and curling up the second hoop member into the outer cylinder simultaneously with the step of curling up the hoop member forming the inner cylinder.

2. A method for manufacturing a motor armature according to claim 1; wherein the step of attaching the second end of each of the pole pieces to the second hoop member comprises the step of successively attaching the second end of respective pole pieces to the second hoop member while curling the first hoop member and the second hoop member.

3. A method for manufacturing a motor armature according to claim 1; wherein the wire piece of each of the pole pieces comprises an inner core formed of a magnetic material having a high saturation magnetic flux density and a skin layer formed around the inner core comprising a magnetic material having a lower saturation magnetic flux density than the core and having higher magnetic permeability than the core, so that the pole pieces formed from the magnetic wire rod undergo a low iron loss when used in the motor.

4. A method for manufacturing a motor armature according to claim 3; wherein the inner core comprises one of low carbon steel and pure iron.

5. A method for manufacturing a motor armature according to claim 3; wherein the skin layer comprises one of Fe—Co alloy, Fe—Ni alloy and amorphous alloy.

6. A method for manufacturing a motor armature according to claim 1; wherein the wire piece has a circular cross section.

7. A method for manufacturing a motor armature according to claim 1; wherein the step of forming the plurality of pole pieces comprises the steps of winding a coil around a single piece of magnetic wire rod and cutting the single piece of wire rod with the coil thereon into a plurality of segments each comprising an individual pole piece.

8. A method for manufacturing a motor armature according to claim 1; wherein the step of forming the plurality of pole pieces comprises the steps of cutting a magnetic wire rod into a plurality of individual pieces and successively winding a single wire formed of a magnetic material around the individual pieces to form a coil around each of the pieces.

9. A method for manufacturing a motor armature according to claim 1; wherein the step of forming the plurality of pole pieces comprises the steps of cutting a magnetic wire rod into a plurality of pieces, successively winding a wire formed of a magnetic material around the individual pieces to form a coil around each of the pieces, the wire being wound in opposite directions in successive pieces, and hooking and pulling the wire from selected coils to obtain connections for a multi-phase armature.

10. A method for manufacturing a motor armature according to claim 1; wherein the step of forming the plurality of pole pieces comprises the steps of cutting a magnetic wire rod into a plurality of pieces, winding a plurality of wires formed of a magnetic material around selected pieces of magnetic wire, so that each piece has a coil formed of a single wire wound therearound, to form a multi-phase armature.

11. A method for manufacturing a motor armature according to claim 1; wherein the step of creating a plurality of pole pieces comprises the step of winding a magnetic wire around a plurality of wire pieces by use of a winding device having a wire feed tube which branches into a pair of tubes including a wire output tube, wherein the wire pieces are disposed between the pair of tubes while the winding device undergoes angular displacement so as to wind the magnetic wire around the wire pieces.

12. A method for manufacturing a motor armature, comprising the steps of:
   a first step of creating a plurality of pole pieces each comprising a coil wound around a wire piece formed of a magnetic material;
   a second step of fixing a first end of each of the plurality of pole pieces created in the first step to an outer peripheral surface of a cylinder formed by curling up a hoop member formed of a magnetic material radially at equal intervals such that the cylinder is an inner cylinder of the motor armature; and
   forming an outer cylinder coaxial with the inner cylinder attached to the pole pieces by fixing a second end of each of the plurality of pole pieces to the outer cylinder after creating the inner cylinder attached to the first end of each of the pole pieces by curling up the hoop member so that the plurality of pole pieces are fixed to the outer peripheral surface of the hoop member in the second step.

13. A method for manufacturing a motor armature according to claim 12; wherein the wire piece of each of the pole pieces comprises an inner core formed of a magnetic material having a high saturation magnetic flux density and a skin layer formed around the inner core comprising a magnetic material having a lower saturation magnetic flux density than the core and having higher magnetic: permeability than the core, so that the pole pieces formed from the magnetic wire rod undergo a low iron loss when used in the motor.

14. A method for manufacturing a motor armature according to claim 13; wherein the inner core comprises one of low carbon steel and pure iron.

15. A method for manufacturing a motor armature according to claim 13; wherein the skin layer comprises one of Fe—Co alloy, Fe—Ni alloy and amorphous alloy.

16. A method for manufacturing a motor armature according to claim 12; wherein the wire piece has a circular cross section.

17. A method for manufacturing a motor armature according to claim 12; wherein the step of forming the plurality of pole pieces comprises the steps of winding a coil around a single piece of magnetic wire rod and cutting the single piece of wire rod with the coil thereon into a plurality of segments each comprising an individual pole piece.

18. A method for manufacturing a motor armature according to claim 12; wherein the step of forming the plurality of pole pieces comprises the steps of cutting a magnetic wire rod into a plurality of individual pieces and successively winding a single wire formed of a magnetic material around the individual pieces to form a coil around each of the pieces.

19. A method for manufacturing a motor armature according to claim 12; wherein the step of forming the plurality of pole pieces comprises the steps of cutting a magnetic wire rod into a plurality of pieces, successively winding a wire formed of a magnetic material around the individual pieces to form a coil around each of the pieces, the wire being wound in opposite directions in successive pieces, and hooking and pulling the wire from selected coils to obtain connections for a multi-phase armature.

20. A method for manufacturing a motor armature according to claim 12; wherein the step of forming the plurality of pole pieces comprises the steps of cutting a magnetic wire rod into a plurality of pieces, winding a plurality of wires formed of a magnetic material around selected pieces of magnetic wire, so that each piece has a coil formed of a single wire wound therearound, to form a multi-phase armature.

21. A method for manufacturing a motor armature according to claim 12; wherein the step of creating a plurality of pole pieces comprises the step of winding a magnetic wire around a plurality of wire pieces by use of a winding device having a wire feed tube which branches into a pair of tubes including a wire output tube, wherein the wire pieces are disposed between the pair of tubes while the winding device undergoes angular displacement so as to wind the magnetic wire around the wire pieces.

22. A method for manufacturing a motor armature comprising the steps of:
   forming a plurality of pole pieces by winding a coil around a magnetic wire piece;

attaching a first end of each of the pole pieces to a first surface of a hoop member formed of a magnetic material;

curling the hoop member having the pole pieces attached thereto into a cylinder so that the pole pieces are fixed to the outside of the cylinder so that the cylinder is an inner cylinder; and attaching an outer cylinder to a second end of the pole pieces.

23. A method for manufacturing a motor armature according to claim 22; wherein the wire piece of each of the pole pieces comprises an inner core formed of a magnetic material having a high saturation magnetic flux density and a skin layer formed around the inner core comprising a magnetic material having a lower saturation magnetic flux density than the core and having higher magnetic permeability than the core, so that the pole pieces formed from the magnetic wire rod undergo a low iron loss when used in the motor.

24. A method for manufacturing a motor armature according to claim 23; wherein the inner core comprises one of low carbon steel and pure iron.

25. A method for manufacturing a motor armature according to claim 23; wherein the skin layer comprises one of Fe—Co alloy, Fe—Ni alloy and amorphous alloy.

26. A method for manufacturing a motor armature according to claim 23; wherein the wire piece has a circular cross section.

27. A method for manufacturing a motor armature according to claim 22; wherein the step of forming the plurality of pole pieces comprises the steps of winding a coil around a single piece of magnetic wire rod and cutting the single piece of wire rod with the coil thereon into a plurality of segments each comprising an individual pole piece.

28. A method for manufacturing a motor armature according to claim 22; wherein the step of forming the plurality of pole pieces comprises the steps of cutting a magnetic wire rod into a plurality of individual pieces and successively winding a single wire formed of a magnetic material around the individual pieces to form a coil around each of the pieces.

29. A method for manufacturing a motor armature according to claim 22; wherein the step of forming the plurality of pole pieces comprises the steps of cutting a magnetic wire rod into a plurality of pieces, successively winding a wire formed of a magnetic material around the individual pieces to form a coil around each of the pieces, the wire being wound in opposite directions in successive pieces, and hooking and pulling the wire from selected coils to obtain connections for a multi-phase armature.

30. A method for manufacturing a motor armature according to claim 22; wherein the step of forming the plurality of pole pieces comprises the steps of cutting a magnetic wire rod into a plurality of pieces, winding a plurality of wires formed of a magnetic material around selected pieces of magnetic wire, so that each piece has a coil formed of a single wire wound therearound, to form a multi-phase armature.

31. A method for manufacturing a motor armature according to claim 22; wherein the step of fixing each of the pole pieces to the hoop member comprises one of the step of spot welding the pole pieces to the hoop member and adhering the pole pieces to the hoop member.

32. A method for manufacturing a motor armature according to claim 22; wherein the step of curling the hoop member is performed before the step of attaching a first end of the pole pieces thereto.

33. A method for manufacturing a motor armature according to claim 22; wherein the step of curling the hoop member is performed after the step of attaching a first end of the pole pieces thereto.

34. A method for manufacturing a motor armature according to claim 33; wherein the outer cylinder comprises a curled up second hoop member, and the step of attaching an outer cylinder to the pole pieces comprises the step of successively attaching the pole pieces to the second hoop member and curling the second hoop member in parallel with the step of curling the first hoop member.

\* \* \* \* \*